(12) United States Patent
Massengill et al.

(10) Patent No.: US 6,290,357 B1
(45) Date of Patent: Sep. 18, 2001

(54) KINETIC VISUAL FIELD APPARATUS AND METHOD

(75) Inventors: R. Kemp Massengill, Leucadia; Richard J. McClure, San Diego, both of CA (US); Johannes Braeuning, Ostfildern (DE)

(73) Assignee: Virtual-Eye.com, Inc., Leucadia, CA (US)

( * ) Notice: Subject to any disclaimer, the term of this patent is extended or adjusted under 35 U.S.C. 154(b) by 0 days.

(21) Appl. No.: 09/535,940

(22) Filed: Mar. 24, 2000

Related U.S. Application Data

(60) Provisional application No. 60/127,404, filed on Mar. 31, 1999.

(51) Int. Cl.[7] ........................................ A61B 3/14
(52) U.S. Cl. ................................................ 351/209
(58) Field of Search .................................. 351/209, 210; 345/7, 8, 156, 157

(56) References Cited

U.S. PATENT DOCUMENTS

| | | | |
|---|---|---|---|
| 5,035,500 | 7/1991 | Rorabaugh et al. | 351/226 |
| 5,061,059 | 10/1991 | Horn | 351/223 |
| 5,325,136 | 6/1994 | Salibello et al. | 351/243 |
| 5,565,949 | 10/1996 | Kasha, Jr. | 351/224 |
| 5,758,651 | 6/1998 | Nygard et al. | 128/741 |
| 5,864,384 | 1/1999 | McClure et al. | 351/224 |
| 5,867,494 | 2/1999 | Krishnaswamy et al. | 370/352 |
| 5,894,338 | 4/1999 | Miehle et al. | 351/200 |
| 5,942,954 | * 8/1999 | Galiana et al. | 351/209 |
| 6,048,065 | 4/2000 | Davis et al. | 351/221 |
| 6,091,378 | * 7/2000 | Richardson et al. | 345/7 |

FOREIGN PATENT DOCUMENTS

| | | |
|---|---|---|
| 0 428 604 | 11/1996 | (EP) . |
| 0850 661 | 7/1998 | (EP) . |
| 0856 333 | 8/1998 | (EP) . |
| 0857 455 | 8/1998 | (EP) . |

OTHER PUBLICATIONS

Alboliras, E.; Transmission of Full–Length Echocardiographic Images over ISDN for Diagnosing Congenital Heart Disease; 1996; Telemedicine Journal, vol. 2, No. 4; pp. 251–258.

Aitsebaomo, A; Psycophysical and Saccadic Information about Direction for Briefly Presented Visual Targets; 1990; Vision Research, vol. 32, No. 9, 1992; pp 1729–1737.

Angood, P.; Internet–based Telemedicine: A Pratical Tool?; Medicine Meets Virtual Reality; 1998; pp. 383–384.

Armstrong, P.; Telemedicine in the United States—A Summary of Operation Programs; Telemedicine—Explorations in the Use of Telecommunications in Health Care; pp. 309–317.

Arnold, D.; TheOoculomotor Integrator: Testing of a Neural Network Mode; Dec. 1995; Experimental Brain Research (1997) 113; pp. 57–74.

Asman, P.; Kinetic and Static Fixation Methods in Automated Threshold Perimetry; 1997; Journal of Glaucoma vol. 8, No. 3, 1999; pp. 290–296.

Baez, K.; Motion Detection Threshold and Field Progression in Normal Tension Glaucoma; Sep. 1994; British Journal of Ophthalmology 1995, vol. 79; pp. 125–128.

Bekker, M.; Exploring Telemedicine—A Look at How This Technology Could Change Your Practice; Sep. 1998; Ophthalmalogy Management; pp. 44–51.

(List continued on next page.)

Primary Examiner—George Manuel
(74) Attorney, Agent, or Firm—Gerald W. Spinks

(57) ABSTRACT

A method and apparatus for testing the visual field of a patient, with a head mounted display, which displays a central fixation icon and a variable peripheral stimulus icon, and which senses the responses of the patient by tracking the gaze of the patient, as the gaze shifts between the central fixation icon and the peripheral stimulus icon.

24 Claims, 4 Drawing Sheets

OTHER PUBLICATIONS

Bethke, W.; The Internet vs. Glaucoma; Nov. 1997; Review of Ophthalmology; p. 19.

Black, H.; Glaucoma—Assess Tests for Visual Function; Mar. 2000; Eyenet; pp. 27–28.

Blackwell, N.; Telemedicine Ophthalmology Consultation in Remote Queensland; Apr., 1997; Medical Journal of Australia, 1997, 167; pp. 583–586.

Brigatti, L.; Automatic Detection of Glaucomatous Visual Field Progression With Neural Networks; Jun. 1997; Arch. Ophthalmol. vol. 115; pp. 725–728.

Brigatti, L.; Neural Network to Identify Glaucoma with Structural and Functional Measurements; Nov. 1995; American Journal of Ophthalmology 1996, vol. 121, No. 5; pp. 511–521.

Bullimore, M.; Motion Perception in Glaucoma; Dec. 1993; Investigative Ophthalomology & Visual Science; vol. 34, No. 13; pp. 3526–3533.

Casson, E.; Temporal Modulation Perimetry: The Effects of Aging and Eccentricity on Sensitvity in Normals; Jul. 1992; Investigative Ophthalmology & Visual Science, Oct. 1993; vol. 34, No. 11; pp. 3096–3102.

Defense Department Awards Telemedicine Ophthalmic Technology Contract; May 1997; Telemedicine and Virtual Reality; p. 53.

Dicon Presents a New Standard in Automated Perimtery; Aug. 1998; Advertising Supplement to Review of Ophthalmology; p. 15A.

Dicon Website; Jun. 2, 2000; http://www.dicon.com/; 12 pages.

Dicon Website; May 21, 2000; http://www.dicon.com/; 24 pages.

Dicon; *Field News,* vol. 6, No. 1; 1999; 4 pages.

Gardner, G.; Automatic Detection of Diabetic Retinopathy Using an Artificial Neural Network; a Screening Tool; 1996; British Journal of Ophthalmology 1996:80; pp. 940–944.

Goldbaum, M.; Interpretation of Automated Perimetry for Glaucoma by Neural Network; Oct. 1990; Investigative Ophthalmology & Visual Science, Aug. 1994, vol. 35, No. 9; pp. 3362–3373.

Grigsby, J.; Effects and Effectiveness of Telemedicine; 1995; Health Care Financing Review, vol. 17, No. 1; pp. 115–133.

Grigsby, J.; Telemedicine: Where It Is and Where It's Going; 1998; Annals of Internal Medicine vol. 129, No. 2; pp. 123–127.

Heneghan, C.; Clinical Interaction the Key to Telemedicine; Jun. 1, 1997; Ophthalmology Times; pp. 7–11.

Heneghan, C.; Ophthalmology Rides Wave of Telemedicine; May 1997; Ophthalmolgy Times; 2 pages.

Heneghan, C.; Teleophthalmology at the New York Eye and Ear Infirmary; Dec. 1996; Telemedicine Today 4(5); pp. 42–44.

Johnson, C.; Displacement Threshold Perimetry in Glaucoma Using a Macintosh Computer System and a 21–inch Monitor; Jul. 1994; Perimetry Update 1994/95 Proceedings of the XIth International Perimetric Society Meeting; pp. 103–110.

Katz, J.; Comparison of Analytic Algorithms for Detecting Glaucomatous Visual Field Loss; Dec. 1991; Arch Ophtalmol. vol. 109; pp. 1684–1689.

Lachenmayr, B.; Diffuse and Localized Glaucomatous Field Loss in Light–sense, Flicker and Resolution Perimetry; Aug. 1990; Graefe's Archive for Clinical and Experimental Ophthalmology(1991)229; pp. 267–273.

Lachenmayr, B.; Light–sense, Flicker and Resolution Perimetry in Glaucoma: A Comparative Study; May 1990; Graefes's Archive of Clinical and Experimental Ophthalmology (1991)229; pp. 246–251.

Levin, L.; Neural Network Differentiation of Optic Neuritis and Anterior Ischaemic Optic Neuropathy; May 1996; British Journal of Ophthalmology 1996:80; pp. 835–839.

Lindberg, D.; Medicine and Health on the Internet; Oct. 1998; JAMA vo. 280, No. 15; pp. 1303–1304.

Marcus, D.; Telemedicine Diagnosis of Eye Disorders by Direct Ophthalmoscopy; Sep. 1997; Ophthalmology, vol. 105, No. 10; pp. 1907–1914.

Mitka, M.; Developing Countries Find Telemedicine Forges Links to More Care and Research; Oct. 1998; JAMA vol. 280, No. 15; pp. 1295–1296.

Morales, J.; Comparison Between Tendency–Oriented Perimetry (TOP) and Octopus Threshold Perimetry; Feb. 1999; Ophthalmology, vol. 107, No. 1, Jan. 2000; pp. 134–142.

Mutlukan, E.; Visual Field Interpretation With a Personal Computer Based Neural Network; 1994; Eye, vol. 8; pp. 321–323.

Nitzkin, J.; Reliability of Telemedicine Examination; 1997; Telemedicine Journal, vol. 3, No. 2; pp. 141–157.

Pedersen, S.; Teleconsultation of Patients With Otorhinolaryngologic Conditions; Mar. 1993; Arch. Otolaryngol Head and Neck Surg., vol. 120, Feb. 1994; pp. 133–136.

Sanders, J.; Challenges to the Implementation of Telemedicine; 1995; Telemedicine Journal, vol. 1, No. 2; pp. 115–123.

Sarasohn–Kahn, J.; Tele–health; 1996; Medical and Healthcare Marketplace Guide, $11^{th}$ Edition; 2 pages.

Schiffman, J.; Practice Makes Perfect: Devising Technical Specs for Tele–ophthalmology; 1997; Telemedicine; 5 pages.

Singer, H.; New Perimetry Algorithm Uses Artificial Intelligence to Shorten Test Time; Nov. 15, 1996; Glaucoma; 2 pages.

Silverman, S.; Motion Perception is Abnormal in Primary Open–Angle Glaucoma and Ocular Hypertension; Apr. 1989; Investigative Ophthalmology & Science, vol. 31, No. 4; pp 722–729.

Smith, D.; Using Frequency Doubling Technology; Oct. 1998; Ophthalmology Management; p. 79.

Spenceley, S.; Visual Field Analysis Using Artificial Neural Networks; Nov. 1993; Ophthal. Physiol. Opt. Jul. 1994, vol. 14; pp. 239–248.

Steinman, S.; Real–time Color–frame Animation for Visual Psycophysics on the Macintosh Computer; 1992; Behavior Research Methods, Instruments & Computers 24(3); pp. 439–452.

Telemedicine Targets Mammographic Services; 1997; Biophotonics International Nov./Dec. 1997; 1 page.

Teleophthalmology Clinic Gets a Workout; Nov. 1997; Telemedicine and Virtual Reality Issue 2.11; p. 132.

Uchida, H.; Detection of Structural Damage From Glaucoma With Confocal Laser Image Analysis; Apr. 1996; Investigative Ophthalmology & Visual Science, Nov. 1996, vol. 37, No. 12; pp. 2393–2401.

Van De Grind, W.; Inhomogeneity and Anisotropies for Motion Detection in the Monocular Visual Field of Human Observers; Mar. 1992; Vision Research vo. 33, No. 8; pp. 1089–1107.

Wall, M.; Random Dot Motion Perimtery in Patients With Glaucoma and in Normal Subjects; May 1995; American Journal of Ophthalmology 1995, vol. 120, No. 5; pp. 587–596.

Wall, M.; Motion Perimetry Identifies Nerve Fiber Bundle-like Defects in Ocular Hypertension; Jan. 1997; Arch. Ophthalmol. vo. 115; pp. 26–33.*

Wong, M.; A Comparison of Tangent Screen, Goldmann, and Humphrey Perimetry in the Detection and Localization of Occipital Lesions; Apr. 1999; Ophthalmology vol. 107, No. 3 Mar. 2000; pp. 527–544.*

* cited by examiner

KINETIC VISUAL FIELD APPARATUS AND METHOD

CROSS REFERENCE TO RELATED APPLICATIONS

This application claims priority from U.S. Provisional Patent Application Ser. No. 60/127,404, filed on Mar. 31, 1999, and entitled "Kintetic Visual Field Apparatus and Method."

STATEMENT REGARDING FEDERALLY SPONSORED RESEARCH OR DEVELOPMENT

Not Applicable

BACKGROUND OF THE INVENTION

1. Field of the Invention

This invention is in the field of devices and methods for testing the visual field characteristics of a patient.

2. Background Art

Visual field testing remains the "gold standard" for diagnosing diseases of the optic nerve and the visual system. Ideally, a visual field testing system would objectively measure the visual field of a patient without any subjective response whatsoever on the part of the patient. However, currently known visual field examinations require great concentration on the part of the patient and can be tedious and frustrating to the point of annoyance. Current techniques involve a globe-type visual field tester, called a "perimeter," such as those manufactured by Humphrey Instruments, Dicon, Octopus, and others. These conventional visual field testers generally require that a patient continuously fixate upon a central point, while lights are displayed sequentially into the peripheral field. When the patient sees the light out of the corner of the eye in the peripheral visual field, the patient responds by pressing a button, or responding verbally, all the while being strictly required to maintain central fixation. Generally, central gaze must be maintained without interruption for up to 10 minutes. This requires maximal concentration by the patient.

BRIEF SUMMARY OF THE INVENTION

The present invention provides a novel and much more "user-friendly" device and method for testing the visual field of a patient suspected of having glaucoma, or other disease affecting the visual system and corresponding neurological pathways. This new invention virtually eliminates the tedium inherently present in conventional perimeter globe-style visual field testers. In the present invention, the patient wears a head-mounted display, with a gaze fixation target. Various visual stimuli, such as icons of various shapes, sizes, colors, and luminosity, are displayed for the patient to observe, at various locations throughout the display. The patient signals his observation of these stimuli only by shifting his gaze from the gaze fixation target to the visual stimuli, then back to the gaze fixation target.

The novel features of this invention, as well as the invention itself, will be best understood from the attached drawings, taken along with the following description, in which similar reference characters refer to similar parts, and in which:

DETAILED DESCRIPTION OF THE INVENTION

Figure 1:
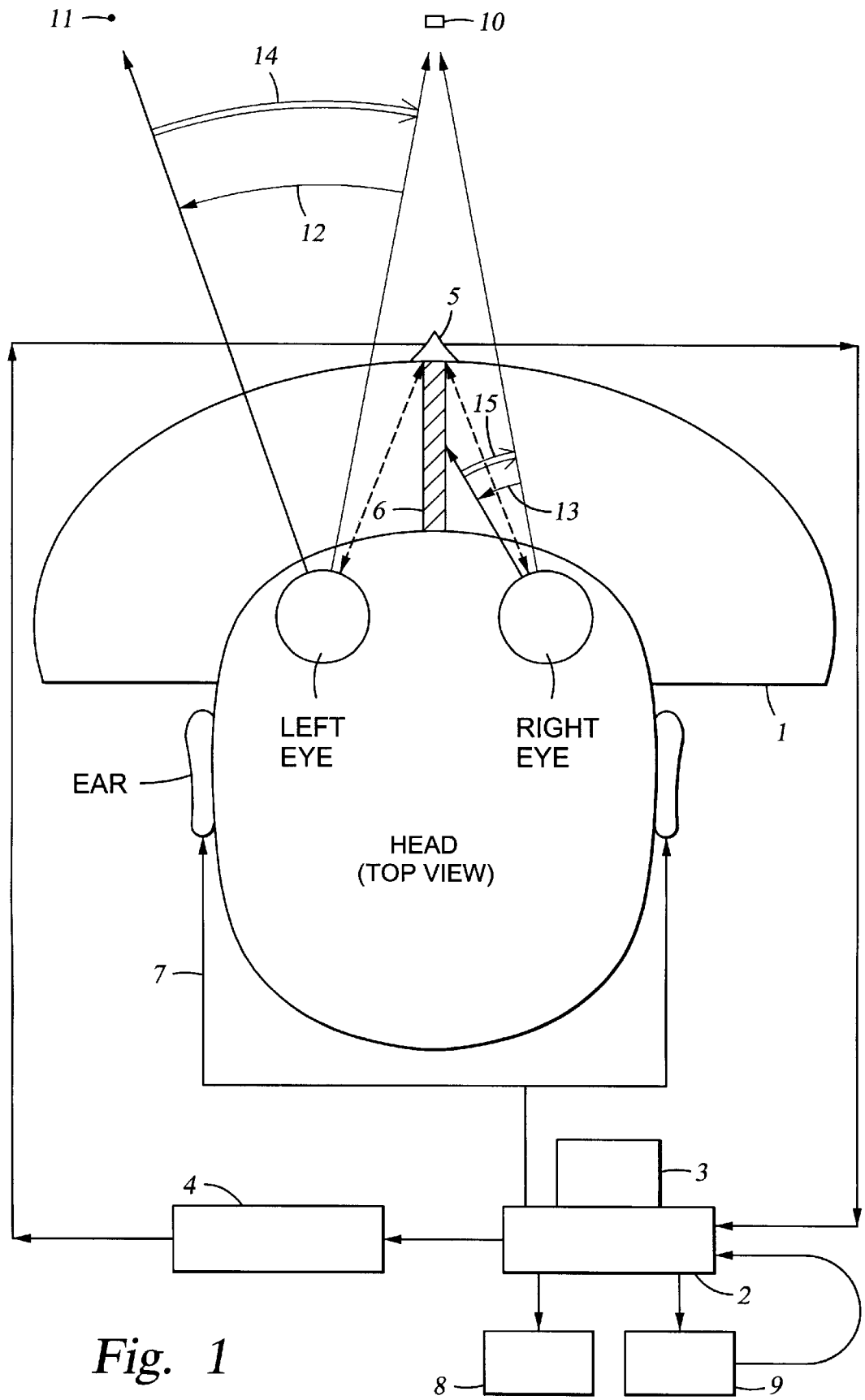
FIG. 1 is a schematic diagram of one embodiment of the apparatus of the present invention, showing a head mounted display controlled by a local computer and controller.

The patient wears a wrap-around "head-mounted display" ("HMD"), which can be in the form of a helmet configuration, or wrap-around goggles or glasses. The visual field testing, then, can be performed in a "virtual-reality" environment. A computer with appropriate software interfaces with the head-mounted display via a controller. In addition to sending signals to the patient, the computer receives incoming response signals from a gaze tracker mounted within the HMD. Also, the computer system provides audio feedback to the patient via headphones or earphones. Such audio cues monitoring the patient's performance eliminate the need for a technician to be continuously involved with the patient during the examination. The system is designed to perform interactively with the patient, in real-time, and, as discussed below, autointerpretation and telemedicine can be utilized.

In the preferred embodiment, the patient is instructed to look at a central fixation target or icon. This central fixation icon remains illuminated and in a stationary position in the center of the patient's visual field throughout the entire visual field test. If desired, the central fixation icon can be made more interesting by such mechanisms as changing the icon's shape or color during the test. An example would be a dot of light, which could change colors, or, alternatively, a spinning disc, which could turn into a small animal. The central fixation icon is on the display during the entire test.

A gaze tracking device mounted in the HMD is utilized to monitor the patient's eye movements to make certain that the patient is, in fact, fixating upon the central fixation icon at the beginning of the test. The gaze tracking device also tracks the eye movements of the patient during the entire visual field examination, relaying this information back to the computer for processing and correlation, such as in comparison with previous visual fields. If desired, the output of the gaze tracking device can provide an input into an autointerpretation system.

After central gaze has been recognized by the computer as having been established, via the gaze tracker, a visible light stimulus is then presented into the peripheral vision of one of the patient's eyes, in the form of a "peripheral stimulus icon".

The patient is instructed to shift fixation from the central fixation icon to the peripheral stimulus icon. The instruction can be as follows: "If you see a light in your side vision, please look at it." The patient is cautioned to look to the side if, and only if, a peripheral stimulus icon is perceived. Otherwise, the patient is instructed to gaze at the central fixation icon.

The gaze tracking device monitors the patient's shift of fixation from the central fixation icon to the peripheral stimulus icon. If the patient's shift of fixation is directly and without equivocation from the central fixation icon to the peripheral stimulus icon, such as in a direct line, rather than random, searching eye movements, this is then transmitted to the computer as a positive response; i.e., the peripheral stimulus icon was perceived as being "seen" by the patient.

The luminosity (brightness), size, color, and shape of the peripheral stimulus icon can vary, so that the test is fully capable of determining the "threshold" visual field; "threshold" meaning when the peripheral stimulus icon is just barely recognized by the patient. To determine thresholds with confidence, repetitive testing is required. Using luminosity as an example, threshold is achieved by beginning with a luminosity level just below what the patient previously perceived, and determining whether this new peripheral stimulus icon ("icon 1") is perceived or not. If not, then a peripheral stimulus icon with slightly greater luminosity ("icon 2") is projected at the identical point within the visual field. If this brighter icon is now perceived, the end-point for luminosity lies in between the first and the second peripheral stimulus icons. The level of luminosity, then, is varied until an "end-point" is achieved. The end-point is defined as the level at which the patient does, in fact, perceive the peripheral stimulus icon, but just barely.

The present invention incorporates such threshold strategies in a head-mounted display, or a virtual reality environment, to perform a kinetic visual field test.

The test is completely automated, and, based upon information received by the computer from the patient, the software within the computer determines the location within the patient's peripheral visual field where the peripheral stimulus icon will be displayed, as well as its luminosity, size, shape, color, etc.

Visual field testing is continued sequentially in the practice of the present invention. When the peripheral stimulus icon is extinguished, the patient signifies recognition of this by returning gaze to the central fixation icon, which, as stated above, remains illuminated throughout the entire test. After the patient resumes central fixation and this state is documented by the computer system, the next peripheral stimulus icon is presented into a different area of the visual field.

The size and intensity of the visual stimulus, or peripheral icon, can be calibrated against "normal" visual fields. The latter are established by measuring and calibrating responses from "normal" patients with "normal" visual fields. These "norms" can be compiled from known visual field data and integrated into the software data bank of the present invention's computer system. Deviations from "normal" will thus be identified by the system's software, and, as described below, such deviations can be autointerpretated via a neural network, or by a rule-based, autointerpretation system.

The visual field of each eye can be displayed on the local computer monitor, and plotted both graphically and numerically (i.e., displaying the number representing the threshold end-points for the peripheral stimulus icons). The printer attached to the computer can print a hard copy of the visual fields, which will then become a permanent record in the patient's chart.

Also, if desired, the visual field can be stored in the computer's hard-drive, or on a separate computer storage disc, and this stored visual field can then become the starting point for the patient's future visual field tests, thus saving time. Also, such computer storage allows instantaneous computerized recognition of changes, however subtle, in the patient's sequential (such as yearly) visual fields, thus minimizing the possibility for human error in recognizing subtle visual field changes which may otherwise go unnoticed.

During the test, the patient is cautioned not to look randomly around the peripheral field searching for dots, but, rather, to look at the peripheral stimulus icon only if this icon is clearly and undeniably perceived. The gaze tracking device will input its signals to the computer, which will ensure that random eye movements are not recorded as positive responses, and such random saccadic movements will be rejected.

Although the central fixation icon is presented to both eyes simultaneously, the peripheral stimulus icon is presented to only one eye at a time. Both eyes can be tested at the same time, however, simply by presenting the peripheral stimulus icon first to one eye, and then to the fellow eye. The sequence from eye to eye can be varied, so that the patient will not anticipate where, or to which eye, the next peripheral stimulus icon will be presented.

The peripheral stimulus icon will "come on" only when gaze fixation has been confirmed by the computer system for a minimum period of time, for instance, 1.5 to 2.0 seconds.

The peripheral stimulus icon will be illuminated for only a rather short period of time, namely, long enough to trigger the mental response and the neurological response to direct the eyes to shift fixation and perceive the peripheral stimulus icon, but not long enough to allow prolonged, random searching eye movements. The length of time for illumination of the peripheral stimulus icon, as well as the time for central fixation maintenance before presentation of the peripheral stimulus icon, can be varied, such that a patient with slow reflexes, such as one with Parkinson's disease, will be given extra response time. Conversely, the "on-times" for both the peripheral stimulus icons and for maintenance of central fixation can be lessened for patients with appropriately fast responses. For patients with extremely fast reflexes, an "ontime" for the peripheral stimulus icon of one second, or even less, can be programmed. Someone with Parkinson's disease, on the other hand, may need an on-time of as long as 5–7 seconds.

The testing is "kinetic," in that the patient's fixation is moving back and forth between the central fixation icon and the peripheral stimulus icons, as the latter are presented throughout the visual field of the patient. It is this change in fixation that is sensed by the gaze tracking system, to signal that the patient has observed the sequentially displayed peripheral stimulus icons. Nothing more is required of the patient than having the patient look at the peripheral stimulus icons, if they are perceived upon presentation. For instance, no buttons need to be pushed by the patient. The present invention, therefore, makes performance of the visual field test extremely simple from the point of view of the patient. With the head-mounted display and the "kinetic" methodology of the present invention, even a paraplegic should be able to perform quite well.

The advantages of the proposed "kinetic" visual field testing invention in a virtual reality environment, with a head mounted display, are many. Fatigue and frustration are minimized, relative to conventional commercial globe-like visual field testers, which obligate the patient to gaze at the central fixation target for minutes on end and ask that the patient not shift fixation to the peripheral stimulus icon. Such shift of fixation with current commercial visual field testers can seriously detract from the test. However, in the present invention, such a shift in fixation is a requirement of the invention; hence, the term "kinetic."

Another advantage of this kinetic visual field testing system, in a head-mounted display and virtual reality environment, is that full body movements and head movements are allowed, which is not the case with conventional, globe-like visual field testing systems. As eye movement is allowed, and, in fact, even demanded, the patient does not experience the tedium associated with conventional testers which mandate that the patient's gaze always be at the central fixation target.

An internal shutter mechanism, or a similar type device, can be employed and integrated within the HMD system, to occlude the fellow eye of the eye being tested. This internal shutter mechanism is operated by the controller in response to signals from the computer. The computer coordinates the shutter mechanism with the presentation of the peripheral stimulus icons and input from the gaze tracker.

A computer with appropriate software directs the controller, which in turn sequentially presents peripheral stimulus icons throughout the visual fields of both eyes, but said presentation is to only one eye at a time.

The peripheral stimulus icons can vary in size, color, luminosity (brightness), shape, and position throughout the patient's visual field. The object is to obtain a threshold visual field for each eye. Threshold means the smallest size, or least bright, peripheral stimulus icon which is perceived unmistakably by the patient.

It should be noted that it is not necessary that the patient focus clearly upon the test stimuli, such as the peripheral stimulus icons or the central fixation icon. What is important, however, is that the area of the retina subserved by a corresponding visual field be adequately defined and measured, and a sharply focused image is not required to do this. Optical aids incorporated within the head-mounted display, or worn in addition to the head-mounted display, are, therefore, optional in the present invention. The omission of such optical aids allows the HMD system to be quite light in weight, thus allowing increased patient comfort.

The visual field test can be performed by utilizing white lights projected upon a bland background, or alternatively, by using colored lights on a colored background, such as blue-on-yellow, or yellow-on-blue. Selection of the appropriate light/background combinations depends upon which combination is considered most efficacious in detecting the earliest states of glaucoma or other neurological diseases.

The central fixation icon has the sole purpose of directing the attention and the gaze of the patient. It is, in effect, an "interest-icon."

A printer attached to the computer delivers a hard-copy record for the patient's chart. The test results can also be stored on the hard disc of the computer, or on a floppy disc or other computer storage disc for future reference. Storage of the test results could be for comparison with future visual fields to ascertain glaucoma progression, for instance, or as a starting point for a followup visual field examination to save time and "wear-and-tear" on the patient.

Another feature which can be incorporated into the present invention is autointerpretation of visual field test results, thereby benefiting from the efficacy of automated data classification systems, such as neural networks, to process visual fields.

Neural nets have great advantages, in that they are unbiased and, as the neural net is "intelligent" and "learns" as the data base enlarges, neural nets have great flexibility. Neural nets, then, by constantly upgrading and becoming more intelligent, maintain state-of-the-art technological readiness as the latest, newest, and most advanced information becomes available and is presented to the neural network.

Alternatively, a rule-based expert data classification autointerpretation system can be used, in which the independent interpretations of experts for a large number of visual fields are reduced to code, and then to explicit "rules," and these codified rules are used to interpret subsequent visual field tests.

Both of these autointerpretation systems are envisioned for use with the present invention. Not only can autointerpretation be performed instantaneously, a tremendous advantage, but recommendations can be made regarding further patient testing, such as CAT-scan, MRI, serial intraocular pressures at different times of the day, intraocular pressure upon dilation of the pupil, and other examinations.

The autointerpretation system of the present invention can be operated locally, that is, within the practitioner's office, or, alternatively, "telemedicine" can be employed. The vehicle of choice for telemedicine is the Internet, which has worldwide capability. A plurality of local testing sites can perform the visual field tests, with test instructions and results being exchanged with a remote central monitoring station, via the Internet. Visual field interpretation can be performed globally by this method, utilizing a remote central monitoring station to service large areas, or even the entire world. Alternatively, several central monitoring stations can be deployed in various countries or geographical areas.

The visual field test is interactively performed, either locally or utilizing telemedicine, with digitized information, including audio, flowing both to and from the patient. Utilizing a telemedicine vehicle, such as the Internet, diagnoses can be formulated and transmitted virtually instantaneously to any location on earth with such telemetric access.

In FIG. 1, software incorporated into the computer 2 transmits digitized signal instructions to the controller 4, which in turn sends said instructions to the gaze tracker 5 incorporated within the head-mounted display 1. The gaze tracker 5 follows eye movements, relaying eye movement responses occurring during the visual field test back to the computer for processing. A shutter mechanism 6 provides an occlusive device. The computer 2 transmits audio instructions to the patient via headphones 7. The test results can be visualized on the monitor 3 associated with the computer 2. A printer 8 connected to the output of the computer 2 can print a hard copy of the test for the patient's permanent record. Additionally, if desired, an autointerpretation system 9, such as a neural network or a rule-based computerized system, can be incorporated into the system, as described above.

The visual field test begins when the central fixation icon 10 is activated. The patient is directed via audio instructions to gaze at the central fixation icon 10, which is seen by both eyes simultaneously in the center of the visual field. Although the central fixation icon 10 is actually incorporated within the head-mounted display 1, it is perceived by the patient in the form of a virtual object in space with a locus outside the head-mounted display 1. The central fixation icon 10 remains "on" during the entire visual field test.

The visual field test continues when a peripheral stimulus icon 11 is presented to one eye or the other, but not to both eyes at the same time. Peripheral stimulus icons 11 can be presented within the head-mounted display 1 anywhere within the visual field of either eye. Similar to the central fixation icon 10, peripheral stimulus icons 11 are illuminated within the physical perimeter of the head-mounted display 1, but are actually perceived by the patient as virtual objects in space located outside the head-mounted display 1. Peripheral stimulus icons 11 do not remain "on" during the entire test, but, rather, are illuminated for only short periods of time. Peripheral stimulus icons 11 are presented sequentially. At no time is more than one peripheral stimulus icon 11 activated, however.

The patient is directed via audio instructions to shift gaze from the central fixation icon 10 to the peripheral stimulus icon 11, if, and only if, such peripheral stimulus icon 11 is unmistakably perceived. The gaze tracker 5 monitors this movement, as represented by the dotted lines, and relays this information back to the computer 2. In the Figure, the left eye is being tested. Note the shift in gaze, as represented by the arrows 12 and 13, from the central fixation icon 10 to the peripheral stimulus icon 11. Occlusion of the fellow, right eye is achieved by the shutter mechanism 6, which prevents the right eye from seeing the peripheral stimulus icon 11 when it is presented in this location of the visual field.

When the peripheral stimulus icon 11 is extinguished, the patient then returns gaze to the central fixation icon 10, which is "on" during the entire test. The return of gaze from the peripheral stimulus icon 11 to the central fixation icon 10 is denoted by the arrows 14 and 15. As noted previously, the patient is instructed to look at the central fixation icon 10 except when a peripheral stimulus icon 11 is distinctly perceived. The complete cycle, then, consists of the patient looking at the central fixation icon 10, then shifting gaze to the peripheral stimulus icon 11, and then returning gaze to the central fixation icon 10.

Figure 2:
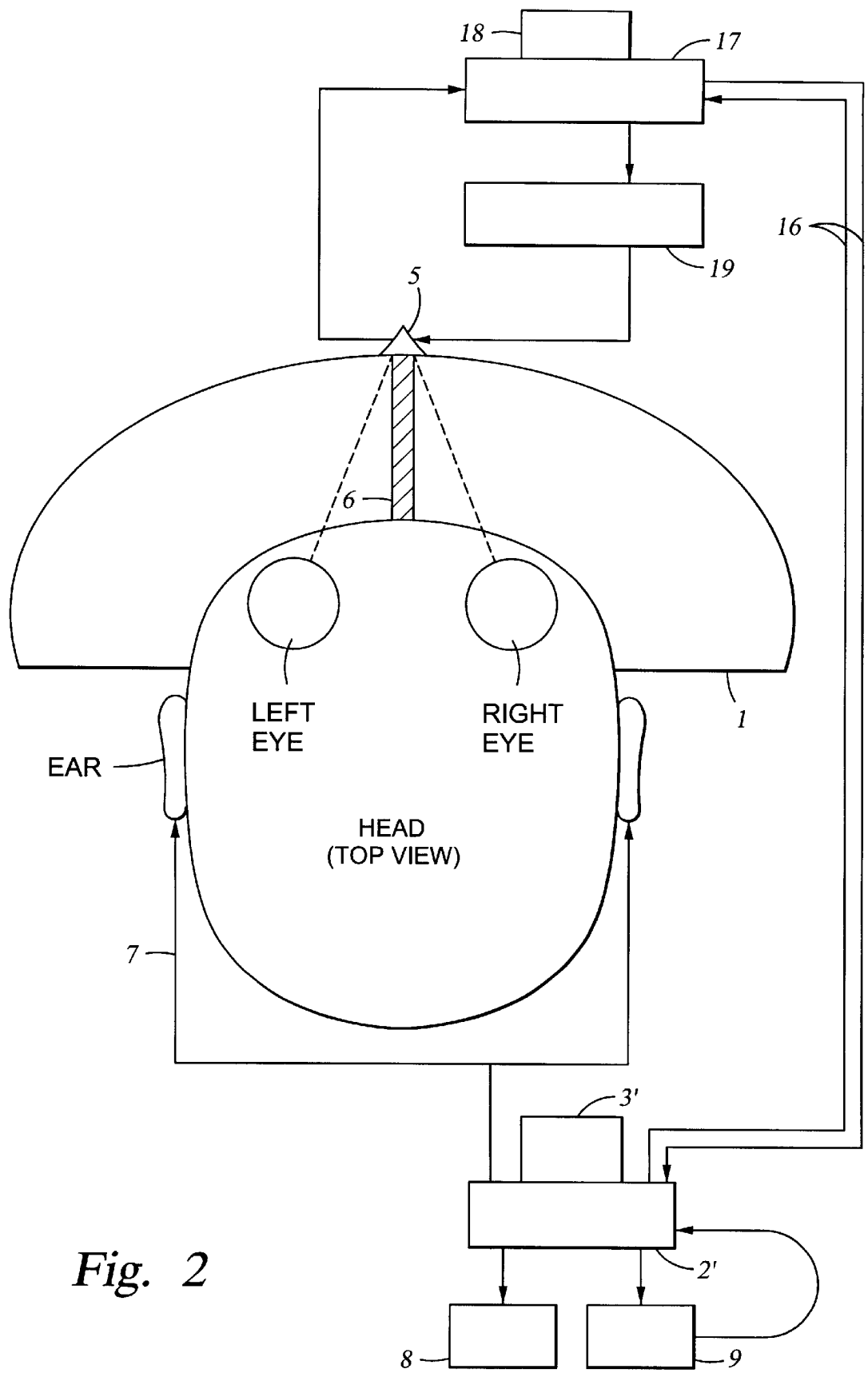
FIG. 2 is a schematic diagram of a second embodiment of the apparatus of the present invention, including a head mounted display controlled by a local computer and controller, and a remote computer, connected via the Internet.

As shown in FIG. 2, telemedicine can be employed, with the Internet, represented by the arrows 16, being the preferred embodiment for this modality. A computer 17 at the local test site, with a monitor 18, receives instructions, via the Internet 16, from a remotely located central computer 2' and transmits the instructions to a local controller 19, which then generates icons on the local head-mounted display 1. Shifts in the patient's gaze are sensed by the gaze tracker 5 and relayed to the local computer 17. These responses are telemetrically relayed back to the remotely located central computer 2 from the local computer 17, via the Internet 16. The visual field test, then, is performed locally, with all instructions, including audio feedback to the patient, originating centrally, at a remote location. An autointerpretation system 9, preferentially performed centrally in this telemedicine model, can be included.

Figure 3:
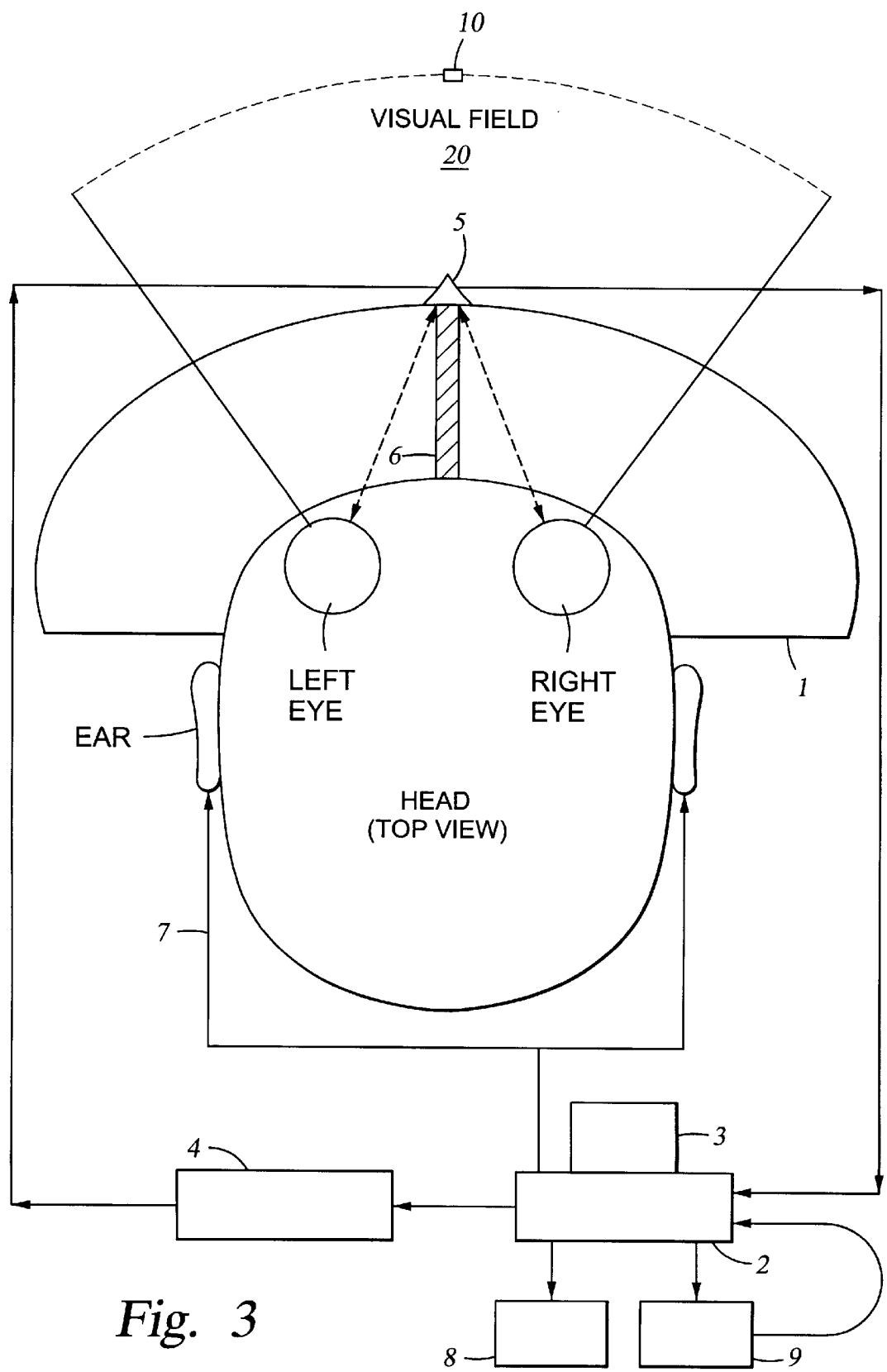
FIG. 3 is a schematic diagram showing the horizontal visual field of the patient, as it relates to the head mounted display of the apparatus of the present invention.
Figure 4:
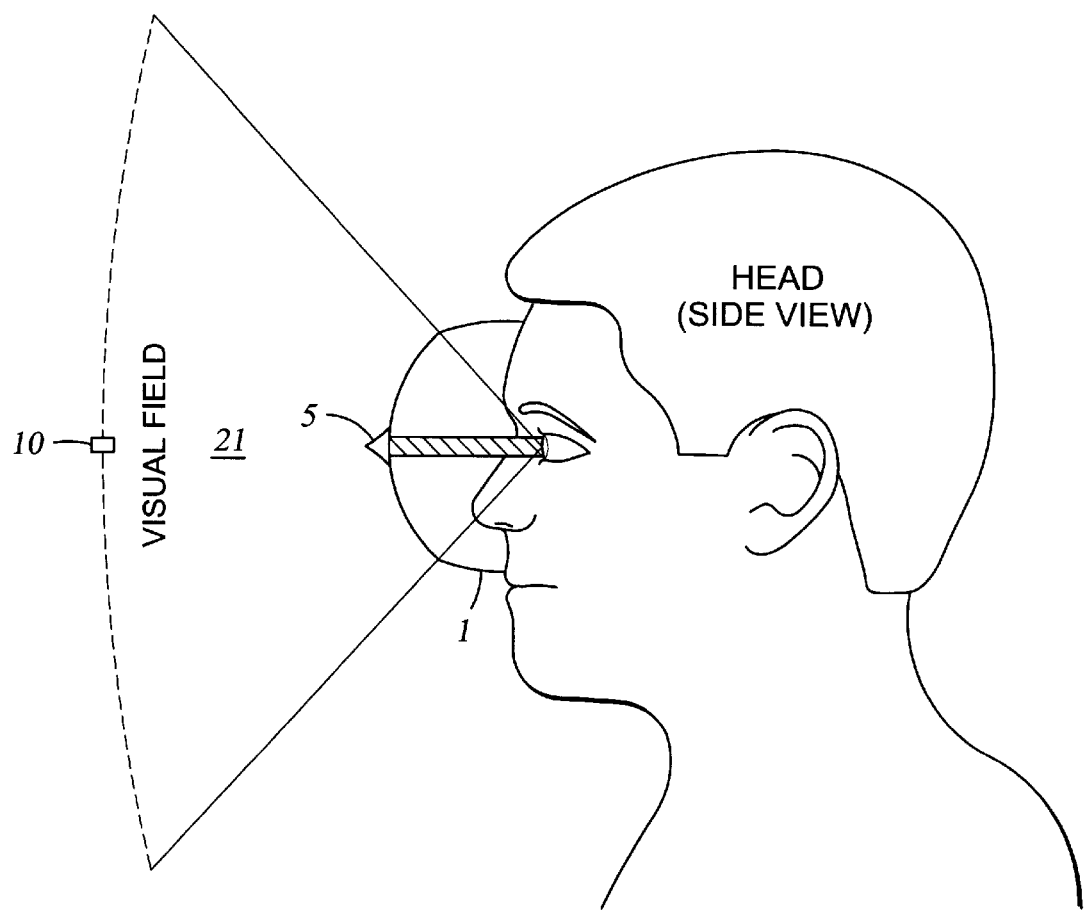
FIG. 4 is a schematic diagram showing the vertical visual field of the patient, as it relates to the head mounted display of the apparatus of the present invention.
Figure 5:
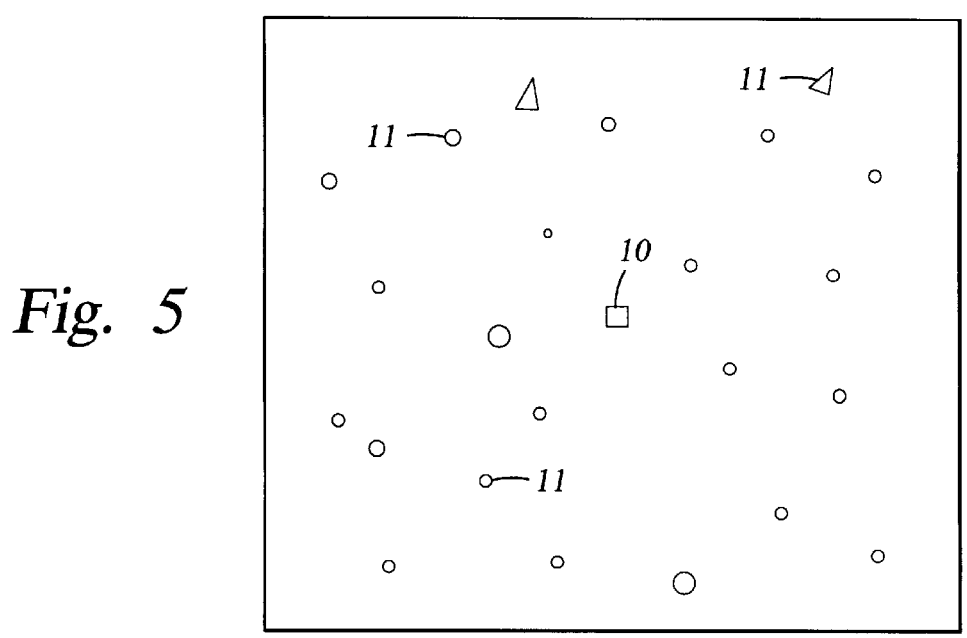
FIG. 5 is a schematic diagram showing various locations, sizes, and shapes for the icons which can be displayed by the apparatus of the present invention.

FIG. 3 shows the horizontal visual field 20. FIG. 4 shows the vertical visual field 21. The vertical and horizontal dimensions of the visual field to be tested are at least as large as those of conventional globe perimeters. The central fixation icon 10 is illuminated throughout the visual field test, while the peripheral stimulus icons 11 are illuminated only one at a time. The peripheral stimulus icons 11, which can vary in size, shape, color, and brightness, are displayed throughout the visual fields of both eyes, but only one eye is tested at a time. FIG. 5 shows the visual field for one eye, illustrating some of the various positions, shapes and sizes in which the icons can be displayed.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

We claim:

1. A visual field testing apparatus comprising:
    a display adapted to be mounted to the head of a patient, for movement with the head;
    a gaze tracking device mounted with said display;
    a computer connected to said display and said gaze tracking device;
    wherein said computer is programmed to generate a gaze fixation target at a selected location on said display;
    wherein said computer is programmed to selectively generate a visual stimulus at any one of a plurality of points on said display; and
    wherein said computer is programmed to detect movement of the patient's gaze between said fixation target and said visual stimulus.

2. The visual field testing apparatus recited in claim 1, further comprising an autointerpretation device connected to said computer for interpreting gaze tracking signals from said computer to evaluate the visual field of a patient.

3. The visual field testing apparatus recited in claim 2, wherein said autointerpretation device comprises a neural network.

4. The visual field testing apparatus recited in claim 2, wherein said autointerpretation device utilizes a rule-based protocol.

5. The visual field testing apparatus recited in claim 1, wherein said computer is located at a local test site, further comprising:
    a remote computer, located remote from said local test site, said remote computer being programmed to input visual stimulus signals into said local computer and to receive gaze tracking signals from said local computer; and
    a data transmission system connecting said local computer to said remote computer.

6. The visual field testing apparatus recited in claim 5, wherein said data transmission system comprises the Internet.

7. The visual field testing apparatus recited in claim 1, wherein said computer is programmed to vary a characteristic of said gaze fixation target.

8. The visual field testing apparatus recited in claim 7, wherein said characteristic is luminosity.

9. The visual field testing apparatus recited in claim 7, wherein said characteristic is size.

10. The visual field testing apparatus recited in claim 7, wherein said characteristic is color.

11. The visual field testing apparatus recited in claim 7, wherein said characteristic is shape.

12. The visual field testing apparatus recited in claim 1, wherein said computer is programmed to vary a characteristic of said visual stimulus.

13. The visual field testing apparatus recited in claim 12, wherein said characteristic is luminosity.

14. The visual field testing apparatus recited in claim 12, wherein said characteristic is size.

15. The visual field testing apparatus recited in claim 12, wherein said characteristic is color.

16. The visual field testing apparatus recited in claim 12, wherein said characteristic is shape.

17. A method for testing the visual field of a patient, said method comprising:
    mounting a display device to the head of a patient, for movement with the head, said display device having a gaze tracking device;
    providing a computer connected to said display and said gaze tracking device;
    generating a gaze fixation target, with said computer, at a selected location on said display;
    sequentially generating a visual stimulus, with said computer, at a plurality of points on said display; and detecting movement of the patient's gaze, with said computer, between said fixation target and said visual stimulus.

18. The method recited in claim 17, further comprising interpreting gaze tracking signals from said computer, with an autointerpretation device, to evaluate the visual field of a patient.

19. The method recited in claim 17, further comprising:

providing a remote computer, located remote from said local test site;

connecting said local computer to said remote computer with a data transmission system;

inputting visual stimulus signals, with said remote computer, into said local computer; and receiving gaze tracking signals, with said remote computer, from said local computer.

20. The method recited in claim 19, wherein said data transmission system comprises the Internet.

21. The method recited in claim 17, further comprising varying a characteristic of said gaze fixation target, with said computer.

22. The method recited in claim 17, further comprising varying a characteristic of said visual stimulus, with said computer.

23. The method recited in claim 17, further comprising interpreting gaze tracking signals from said computer, with a neural network, to evaluate the visual field of a patient.

24. The method recited in claim 17, further comprising interpreting gaze tracking signals from said computer, with an autointerpretation device utilizing a rule-based protocol, to evaluate the visual field of a patient.

* * * * *